(12) United States Patent
Herron et al.

(10) Patent No.: US 6,368,997 B2
(45) Date of Patent: *Apr. 9, 2002

(54) FISCHER-TROPSCH PROCESSES AND CATALYSTS USING FLUORIDED SUPPORTS

(75) Inventors: Norman Herron, Newark; Leo E. Manzer, Wilmington, both of DE (US); Munirpallam A. Subramanian, Kennett Sq., PA (US)

(73) Assignee: Conoco Inc., Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/314,921

(22) Filed: May 19, 1999

Related U.S. Application Data

(60) Provisional application No. 60/086,372, filed on May 22, 1998, provisional application No. 60/097,180, filed on Aug. 20, 1998, and provisional application No. 60/086,405, filed on May 22, 1998.

(51) Int. Cl.[7] .......................... C07C 27/00; B01J 23/40; B01J 23/00; B01J 27/128; B01J 27/13

(52) U.S. Cl. .................. 502/302; 502/326; 502/327; 502/229; 502/230; 518/700; 518/701; 518/713; 518/714; 518/715; 518/716; 518/717; 518/718; 518/719; 518/721

(58) Field of Search .................. 502/302, 326, 502/327, 229, 230; 518/700, 701, 713–719, 721

(56) References Cited

U.S. PATENT DOCUMENTS

| | | | |
|---|---|---|---|
| 3,268,439 A | 8/1966 | Tupman et al. | 208/112 |
| 3,619,412 A | 11/1971 | Clement et al. | 208/111 |
| 3,711,399 A | 1/1973 | Estes et al. | 208/112 |
| 4,088,671 A | 5/1978 | Kobylinski | 260/449.6 |
| 4,275,046 A | 6/1981 | McVicker et al. | 423/258 |
| 4,413,064 A | 11/1983 | Beuther et al. | 518/715 |
| 4,477,595 A | 10/1984 | Madon | 518/715 |
| 4,513,104 A | 4/1985 | Wright et al. | 518/714 |
| 4,542,122 A * | 9/1985 | Payne et al. | 502/325 |
| 4,565,803 A * | 1/1986 | Schoenthal et al. | 502/303 |
| 4,565,831 A * | 1/1986 | Wright et al. | 518/700 |
| 4,568,663 A * | 2/1986 | Mauldin | 502/325 |
| 4,619,910 A | 10/1986 | Dyer et al. | 502/336 |
| 4,659,681 A | 4/1987 | Rice et al. | 502/5 |
| 4,663,305 A * | 5/1987 | Mauldin et al. | 502/304 |
| 4,670,472 A | 6/1987 | Dyer et al. | 518/700 |
| 4,681,867 A | 7/1987 | Dyer et al. | 502/242 |
| 4,766,260 A * | 8/1988 | Manzer et al. | 570/168 |
| 4,832,819 A | 5/1989 | Hamner | 208/27 |
| 4,902,838 A | 2/1990 | Manzer et al. | 570/151 |
| 4,919,786 A | 4/1990 | Hamner et al. | 208/27 |
| 4,923,841 A | 5/1990 | Hamner et al. | 502/230 |
| 4,943,672 A | 7/1990 | Hamner et al. | 585/737 |
| 5,057,470 A * | 10/1991 | Kellner | 502/35 |
| 5,221,720 A * | 6/1993 | McDaniel et al. | 526/135 |
| 5,243,106 A | 9/1993 | Manzer et al. | 570/166 |
| 5,248,701 A | 9/1993 | Soled et al. | 518/700 |
| 5,348,982 A | 9/1994 | Herbolzheimer et al. | 518/700 |
| 5,393,509 A | 2/1995 | Corbin et al. | 423/465 |
| 5,417,954 A | 5/1995 | Harlow et al. | 423/465 |
| 5,460,795 A | 10/1995 | Corbin et al. | 423/465 |
| 5,545,674 A * | 8/1996 | Behrmann et al. | 518/715 |
| 5,559,069 A | 9/1996 | Rao et al. | 502/226 |
| 5,866,730 A * | 2/1999 | Rao | 570/178 |
| 5,900,159 A | 5/1999 | Engel et al. | 210/788 |
| 5,919,994 A * | 7/1999 | Rao | 570/176 |
| 5,932,776 A * | 8/1999 | Cheminal et al. | 570/168 |
| 5,945,573 A * | 8/1999 | Nappa et al. | 570/175 |
| 5,981,608 A | 11/1999 | Geerlings et al. | 518/715 |
| 6,103,099 A * | 8/2000 | Wittenbrink et al. | 208/27 |

FOREIGN PATENT DOCUMENTS

| | | |
|---|---|---|
| DE | 731295 | 8/1936 |
| EP | 142887 | 6/1986 |
| EP | 497436 | 8/1992 |
| WO | WO 9719751 | 11/1996 |
| WO | WO 9847620 | 10/1998 |

OTHER PUBLICATIONS

PCT Notification of Transmittal of the International Search Report or the Declaration dated Apr. 11, 2000.
PCT International Search Report dated Oct. 15, 1999.
E. Iglesia et al. 1993; In: "Computer–Aided Design of Catalysts," ed. E. R. Becker et al., p. 215, New York, Marcel Dekker, Inc.). Month not available.
N. Herron et al. 1993, "Organic Cation Salts of the Tetrafluoroaluminate Anion . . . " J. Am. Chem. Soc. 115:3028–3029, Jan. 1993.

* cited by examiner

*Primary Examiner*—Mark L. Bell
*Assistant Examiner*—Patricia L. Hailey
(74) *Attorney, Agent, or Firm*—Conley, Rose & Tayon, PC

(57) ABSTRACT

A process is disclosed for producing hydrocarbons. The process involves contacting a feed stream comprising hydrogen and carbon monoxide with a catalyst in a reaction zone maintained at conversion-promoting conditions effective to produce an effluent stream comprising hydrocarbons. In accordance with this invention the catalyst used in the process includes at least one catalytic metal selected for Fischer-Tropsch reactions (e.g., iron, cobalt, nickel and/or ruthenium); and a support selected from the group consisting of fluorides and fluorided oxides of at least one element selected from the elements of Groups 2 through 15 of the periodic table of elements and elements with atomic numbers 58 through 71 (e.g., zinc, magnesium, calcium, barium, chromium, yttrium, lanthanum, samarium, europium and/or dysprosium).

20 Claims, No Drawings

FISCHER-TROPSCH PROCESSES AND CATALYSTS USING FLUORIDED SUPPORTS

CROSS-REFERENCE TO RELATED APPLICATIONS

This application claims the benefit of U.S. provisional patent application Serial No. 60/086,372, filed May 22, 1998, U.S. provisional patent application Serial No. 60/097,180, filed Aug. 20, 1998, U.S. provisional patent application Serial No. 60/086,405, filed May 22, 1998, all of which are incorporated herein by reference in their entirety.

STATEMENT REGARDING FEDERALLY SPONSORED RESEARCH OR DEVELOPMENT

Not applicable.

FIELD OF THE INVENTION

The present invention relates to a process for the preparation of hydrocarbons from synthesis gas, i.e., a mixture of carbon monoxide and hydrogen, typically labeled the Fischer-Tropsch process. Particularly, this invention relates to the use of metal fluoride supported catalysts for the Fischer-Tropsch process.

BACKGROUND OF THE INVENTION

Large quantities of methane, the main component of natural gas, are available in many areas of the world. Methane can be used as a starting material for the production of other hydrocarbons. The conversion of methane to hydrocarbons is typically carried out in two steps. In the first step methane is reformed with water or partially oxidized with oxygen to produce carbon monoxide and hydrogen (i.e., synthesis gas or syngas). In a second step, the syngas is converted to hydrocarbons.

This second step, the preparation of hydrocarbons from synthesis gas is well known in the art and is usually referred to as Fischer-Tropsch synthesis, the Fischer-Tropsch process, or Fischer-Tropsch reaction(s). Catalysts for use in such synthesis usually contain a catalytically active metal of Groups 8, 9, 10 (in the New notation of the periodic table of the elements, which is followed throughout). In particular, iron, cobalt, nickel, and ruthenium have been abundantly used as the catalytically active metals. Cobalt and ruthenium have been found to be most suitable for catalyzing a process in which synthesis gas is converted to primarily hydrocarbons having five or more carbon atoms (i.e., where the $C_5^+$ selectivity of the catalyst is high).

The Fischer-Tropsch reaction involves the catalytic hydrogenation of carbon monoxide to produce a variety of products ranging from methane to higher alkanes and aliphatic alcohols. The methanation reaction was first described in the early 1900's, and the later work by Fischer and Tropsch dealing with higher hydrocarbon synthesis was described in the 1920's.

The Fischer-Tropsch synthesis reactions are highly exothermic and reaction vessels must be designed for adequate heat exchange capacity. Because the feed streams to Fischer-Tropsch reaction vessels are gases while the product streams include liquids and waxes, the reaction vessels must have the ability to continuously produce and remove the desired range of liquid and wax hydrocarbon products. The process has been considered for the conversion of carbonaceous feedstock, e.g., coal or natural gas, to higher value liquid fuel or petrochemicals. The first major commercial use of the Fischer-Tropsch process was in Germany during the 1930's. More than 10,000 B/D (barrels per day) of products were manufactured with a cobalt based catalyst in a fixed-bed reactor. This work has been described by Fischer and Pichler in Ger. Pat. No. 731,295 issued Aug. 2, 1936.

Motivated by production of high-grade gasoline from natural gas, research on the possible use of the fluidized bed for Fischer-Tropsch synthesis was conducted in the United States in the mid-1940s. Based on laboratory results, Hydrocarbon Research, Inc. constructed a dense-phase fluidized bed reactor, the Hydrocol unit, at Carthage, Texas, using powdered iron as the catalyst. Due to disappointing levels of conversion, scale-up problems, and rising natural gas prices, operations at this plant were suspended in 1957. Research has continued, however, on developing Fischer-Tropsch reactors such as slurry-bubble columns, as disclosed in U.S. Pat. No. 5,348,982 issued Sep. 20, 1994.

Commercial practice of the Fischer-Tropsch process has continued from 1954 to the present day in South Africa in the SASOL plants. These plants use iron-based catalysts, and produce gasoline in relatively high-temperature fluid-bed reactors and wax in relatively low-temperature fixed-bed reactors.

Research is likewise continuing on the development of more efficient Fischer-Tropsch catalyst systems and reaction systems that increase the selectivity for high-value hydrocarbons in the Fischer-Tropsch product stream. In particular, a number of studies describe the behavior of iron, cobalt or ruthenium based catalysts in various reactor types, together with the development of catalyst compositions and preparations.

There are significant differences in the molecular weight distributions of the hydrocarbon products from Fischer-Tropsch reaction systems. Product distribution or product selectivity depends heavily on the type and structure of the catalysts and on the reactor type and operating conditions. Accordingly, it is highly desirable to maximize the selectivity of the Fischer-Tropsch synthesis to the production of high-value liquid hydrocarbons, such as hydrocarbons with five or more carbon atoms per hydrocarbon chain.

U.S. Pat. No. 4,659,681 issued on Apr. 21, 1987, describes the laser synthesis of iron based catalyst particles in the 1–100 micron particle size range for use in a slurry reactor for Fischer-Tropsch synthesis.

U.S. Pat. No. 4,619,910 issued on Oct. 28, 1986, and U.S. Pat. No. 4,670,472 issued on Jun. 2, 1987, and U.S. Pat. No. 4,681,867 issued on Jul. 21, 1987, describe a series of catalysts for use in a slurry Fischer-Tropsch process in which synthesis gas is selectively converted to higher hydrocarbons of relatively narrow carbon number range. Reactions of the catalyst with air and water and calcination are specifically avoided in the catalyst preparation procedure. The catalysts are activated in a fixed-bed reactor by reaction with $CO+H_2$ prior to slurrying in the oil phase in the absence of air.

Catalyst supports for catalysts used in Fischer-Tropsch synthesis of hydrocarbons have typically been oxides (e.g., silica, alumina, titania, zirconia or mixtures thereof, such as silica-alumina). It has been claimed that the Fischer-Tropsch synthesis reaction is only weakly dependent on the chemical identity of the metal oxide support (see E. Iglesia et al. 1993, In: "Computer-Aided Design of Catalysts," ed. E. R. Becker et al., p. 215, New York, Marcel Dekker, Inc.). The hydrocarbon products prepared by using these catalysts usually have a very wide range of molecular weights.

U.S. Pat. No. 4,477,595 discloses ruthenium on titania as a hydrocarbon synthesis catalyst for the production of $C_5$ to $C_{40}$ hydrocarbons, with a majority of paraffins in the $C_5$ to $C_{20}$ range. U.S. Pat. No. 4,542,122 discloses a cobalt or cobalt-thoria on titania having a preferred ratio of rutile to anatase, as a hydrocarbon synthesis catalyst U.S. Pat. No. 4,088,671 discloses a cobalt-ruthenium catalyst where the support can be titania but preferably is alumina for economic reasons. U.S. Pat. No. 4,413,064 discloses an alumina supported catalyst having cobalt, ruthenium and a Group 3 or Group 4 metal oxide, e.g., thoria. European Patent No. 142,887 discloses a silica supported cobalt catalyst together with zirconium, titanium, ruthenium and/or chromium.

Despite the vast amount of research effort in this field, Fischer-Tropsch catalysts using metal fluoride supports are not known in the art. There is still a great need to identify new catalysts for Fischer-Tropsch synthesis; particularly catalysts that provide high $C_5^+$ hydrocarbon selectivities to maximize the value of the hydrocarbons produced and thus the process economics.

SUMMARY OF THE INVENTION

This invention provides a process and catalyst for producing hydrocarbons, and a method for preparing the catalyst. The process comprises contacting a feed stream comprising hydrogen and carbon monoxide with a catalyst in a reaction zone maintained at conversion-promoting conditions effective to produce an effluent stream comprising hydrocarbons. In accordance with this invention the catalyst used in the process comprises at least one catalytic metal for Fischer-Tropsch reactions (e.g., at least one metal selected from the group consisting of iron, cobalt, nickel and ruthenium); and a support material selected from the group consisting of fluorides and fluorided oxides of at least one element selected from a group of elements including the elements of Groups 2 through 15 of the periodic table of elements, and the elements with atomic numbers 58 through 71 (the Lanthanide series of elements, e.g., zinc, magnesium, calcium, barium, chromium, yttrium, lanthanum, samarium, europium and/or dysprosium).

The invention also includes a process for producing hydrocarbons, comprising contacting a feed stream comprising hydrogen and carbon monoxide with a catalyst in a reaction zone maintained at conversion-promoting conditions effective to produce an effluent stream comprising hydrocarbons; said catalyst comprising at least one catalytic metal for Fischer-Tropsch reactions; and a support selected from the group consisting of fluorides and fluorided oxides of at least one element selected from the group consisting of the elements of Group 2 through 15 of the periodic table of elements and the Lanthanide series of elements (the elements with atomic numbers 58 through 71).

The invention also includes a method for the preparation of a supported Fischer-Tropsch catalyst comprising fluoriding a support selected from the group consisting of at least one element of Group 2 through 15 of the periodic table of elements and elements with atomic number 58 though 71, and their oxide forms, supporting a catalytically active metal for Fischer-Tropsch reactions on the fluorided support, reducing the supported catalyst.

DETAILED DESCRIPTION OF THE INVENTION

The feed gases charged to the process of the invention comprise hydrogen, or a hydrogen source, and carbon monoxide. $H_2/CO$ mixtures suitable as a feedstock for conversion to hydrocarbons according to the process of this invention can be obtained from light hydrocarbons such as methane by means of steam reforming, partial oxidation, or other processes known in the art. Preferably the hydrogen is provided by free hydrogen, although some Fischer-Tropsch catalysts have sufficient water gas shift activity to convert some water to hydrogen for use in the Fischer-Tropsch process. It is preferred that the molar ratio of hydrogen to carbon monoxide in the feed be greater than 0.5:1 (e.g., from about 0.67 to 2.5). Preferably, when cobalt, nickel and/or ruthenium catalysts are used the feed gas stream contains hydrogen and carbon monoxide in a molar ratio of about 2:1; and preferably when iron catalysts are used the feed gas stream contains hydrogen and carbon monoxide in a molar ratio of about 0.67:1. The feed gas may also contain carbon dioxide. The feed gas stream should contain a low concentration of compounds or elements that have a deleterious effect on the catalyst, such as poisons. For example, the feed gas may need to be pre-treated to ensure that it contains low concentrations of sulfur or nitrogen compounds such as hydrogen sulfide, ammonia and carbonyl sulfides.

The feed gas is contacted with the catalyst in a reaction zone. Mechanical arrangements of conventional design may be employed as the reaction zone including, for example, fixed bed, fluidized bed, slurry phase, slurry bubble column, reactive distillation column, or ebullating bed reactors, among others, may be used. Accordingly, the size and physical form of the catalyst particles may vary depending on the reactor in which they are to be used.

A component of the catalysts used in this invention is the support material, which carries the active catalyst component. The support or carrier can comprise a fluoride of an element of Group 2 through Group 15 or a fluoride of a Lanthanide series element (an element having an atomic number of 58 through 71). Preferred are fluoride supports selected from the group consisting of zinc fluoride, magnesium fluoride, calcium fluoride, barium fluoride, chromium fluoride, yttrium fluoride, lanthanum fluoride, samarium fluoride, europium fluoride and/or dysprosium fluoride (which are commercially available).

The fluorided support material can also be prepared from at least one oxide of an element of Group 2 through Group 15 or from at least one oxide of an element having an atomic number 58 through 71. The Group 2 elements include Mg, Ca, Sr and Ba; the Group 3 elements include Sc, Y and La; the Group 4 elements include Ti, Zr and Hf; the Group 5 elements include V, Nb and Ta; the Group 6 elements include Cr, Mo and W; the Group 7 elements include Mn and Re; the Group 8 elements include Fe and Ru; the Group 9 elements include Co, Rh and Ir; the Group 10 elements include Ni, Pd and Pt; the Group 11 elements include Cu, Ag and Au; the Group 12 elements include Zn and Cd; the Group 13 elements include Ga, In and Ti; the Group 14 elements include Ge, Sn and Pb; and the Group 15 elements include P, Sb, and Bi. Elements with atomic numbers of 58 to 71 (the Lanthanide series of elements) include Ce, Pr, Nd, Sm, Eu, Gd, Tb, Dy, Ho, Er, TM, Yb, and Lu.

Preferred are oxides of metals selected from the group consisting of Zn, Mg, Ca, Ba, Cr, Y, La, Sm, Eu and Dy. The oxide can be fluorinated to a desired fluorine content by treating one of the above at least one metal oxides with a fluorine-containing compound at an elevated temperature, e.g., at about 200° C. to about 450° C. A pretreatment with a vaporizable fluorine-containing compound such as HF, $CCl_3F$, $CCl_2F_2$, $CHF_3$, $CHClF_2$, $CH_3CHF_2$ or $CCl_2FCClF_2$ can be done in any convenient manner. (Compare e.g., U.S. Pat. Nos. 4,275,046 and 4,902,838 and 5,243,106, which are incorporated herein by reference in their entirety.)

A vaporizable fluorine-containing compound is defined as a fluorine-containing compound which, when passed over the support at the indicated conditions, will fluorinate the support to the desired degree. The atomic ratio of fluorine to oxygen for the above fluorided oxides can vary over a wide range, but is normally at least 0.001:1. Oxides that have been treated with fluosilicic acid ($H_2SiF_6$) in a manner analogous to the treatment of alumina as described in European Patent Application No. EP 497,436 can also be used as a support.

Another component of the catalyst of the present invention is the catalytic metal. Preferably, the catalytic metal is selected from iron, cobalt, nickel and/or ruthenium. Normally, the metal component is reduced to provide elemental metal (e.g., elemental iron, cobalt, nickel and/or ruthenium) before use. The catalyst must contain a catalytically effective amount of the metal component(s). The amount of catalytic metal present in the catalyst may vary widely. Typically, the catalyst comprises about 1 to 50% by weight (as the metal) of total supported iron, cobalt, nickel and/or ruthenium per total weight of the catalytic metal and support, preferably about 1 to 30% by weight, and still more preferably about 1 to 10% by weight. Each of the metals can be used individually or in combination, especially cobalt and ruthenium. One preferred catalyst comprises about 20% by weight of a combination of cobalt and ruthenium where the ruthenium content is from about 0.001 to about 1 weight %.

The catalyst may also comprise one or more additional promoters or modifiers known to those skilled in the art. When the catalytic metal is iron, cobalt, nickel, and/or ruthenium, suitable promoters include at least one promoter selected from the group consisting of Group 1 metals (i.e., Na, K, Rb, Cs), Sr, Group 11 metals (i.e., Cu, Ag, and Au) Sc, Group 4 metals (i.e., Ti, Zr and Hf), Group S metals (i.e., V, Nb and Ta), and Rh, Pd, Os, Ir, Pt and Re. Preferably, any additional promoters for the cobalt and/or ruthenium catalysts are selected from Sc, Ti, Zr, Hf, Rh, Pd, Os, Ir, Pt, Re, Nb, Cu, Ag and Ta. Preferably, any additional promoters for the iron catalysts are selected from Na, K, Rb, Cs and Sr. The amount of additional promoter, if present, is typically between 0.001 and 40 parts by weight per 100 parts of carrier.

By fluorided oxide of an element is meant a composition comprising oxygen, fluorine, and the element. The fluorine content of the fluorided oxide can vary over a wide range. Fluorided oxides containing from 0.001% to about 10% by weight fluorine are preferred. The remainder of the fluorided oxide component will include oxygen and the element. The composition may also contain a minor amount (compared to the metal) of silicon and phosphorus. A catalyst comprising cobalt (e.g., 20% by weight) supported on a fluorided titania/alumina is most preferred.

The catalysts of the present invention may be prepared by any of the methods known to those skilled in the art. By way of illustration and not limitation, such methods include impregnating the catalytically active compounds or precursors onto a support, extruding one or more catalytically active compounds or precursors together with support material to prepare catalyst extrudates, and/or precipitating the catalytically active compounds or precursors onto a support. Accordingly, the supported catalysts of the present invention may be used in the form of powders, particles, pellets, monoliths, honeycombs, packed beds, foams, and aerogels.

The most preferred method of preparation may vary among those skilled in the art depending, for example, on the desired catalyst particle size. Those skilled in the art are able to select the most suitable method for a given set of requirements.

One method of preparing supported metal catalyst (e.g., a cobalt on lanthanum fluoride) is by incipient wetness impregnation of the support with an aqueous solution of a soluble metal salt such as nitrate, acetate, acetylacetonate or the like. Another method includes preparing the supported metal catalyst from a molten metal salt. One preferred method is to impregnate the support with a molten metal nitrate (e.g., $Co(NO_3)_2.6H_2O$). Alternatively, a supported metal catalyst can be prepared from a zero valent metal precursor. One preferred method is to impregnate the support with a solution of zero valent cobalt such as $Co_2(CO)_8$, $Co_4(CO)_{12}$ or the like in an organic solvent (e.g., toluene). The impregnated support is dried and reduced with a hydrogen containing gas. The hydrogen reduction step may not be necessary if the catalyst is prepared with zero valent cobalt. In another preferred method, the impregnated support is dried, oxidized with air or oxygen and reduced with a hydrogen containing gas.

Typically, at least a portion of the metal(s) of the catalytic metal component of the catalysts of the present invention is present in a reduced state (i.e., in the metallic state). Therefore, it is normally advantageous to activate the catalyst prior to use by a reduction treatment in the presence of hydrogen at an elevated temperature. Typically, the catalyst is treated with hydrogen at a temperature in the range of from about 75° C. to about 500° C., for about 0.5 to about 24 hours at a pressure of about 1 to about 75 atm. Pure hydrogen may be used in the reduction treatment, as may a mixture of hydrogen and an inert gas such as nitrogen, or a mixture of hydrogen and other gases as are known in the art, such as carbon monoxide and carbon dioxide. Reduction with pure hydrogen and reduction with a mixture of hydrogen and carbon monoxide are preferred. The amount of hydrogen may range from about 1% to about 100% by volume.

The Fischer-Tropsch process is typically run in a continuous mode. In this mode, typically, the gas hourly space velocity through the reaction zone may range from about 100 volumes/hour/volume catalyst (v/hr/v) to about 10,000 v/hr/v, preferably from about 300 v/hr/v to about 2,000 v/hr/v. The reaction zone temperature is typically in the range from about 160° C. to about 300° C. Preferably, the reaction zone is operated at conversion promoting conditions at temperatures from about 190° C. to about 260° C. The reaction zone pressure is typically in the range of about 80 psig (653 kPa) to about 1000 psig (6994 kPa), preferably, from 80 psig (653 kPa) to about 600 psig (4237 kPa), and still more preferably, from about 140 psig (1066 kPa) to about 400 psig (2858 kPa).

The products resulting from the process will have a great range of molecular weights. Typically, the carbon number range of the product hydrocarbons will start at methane and continue to the limits observable by modem analysis, about 50 to 100 carbon atoms per molecule. The process is particularly useful for making hydrocarbons having five or more carbon atoms, especially when the above-referenced preferred space velocity, temperature, and pressure ranges are employed.

The wide range of hydrocarbons produced in the reaction zone will typically afford liquid phase products at the reaction zone operating conditions. Therefore the effluent stream of the reaction zone will often be a mixed phase stream including liquid and vapor phase products. The effluent stream of the reaction zone may be cooled to effect the condensation of additional amounts of hydrocarbons and passed into a vapor-liquid separation zone separating the liquid and vapor phase products. The vapor phase material may be passed into a second stage of cooling for recovery of additional hydrocarbons. The liquid phase material from the initial vapor-liquid separation zone together with any liquid from a subsequent separation zone may be fed into a fractionation column. Typically, a stripping column is employed first to remove light hydrocarbons such as propane and butane. The remaining hydrocarbons may be passed into a fractionation column where they are separated by boiling point range into products such as naphtha, kerosene and fuel oils. Hydrocarbons recovered from the reaction zone and having a boiling point above that of the desired products may be passed into conventional processing equipment such as a hydrocracking zone in order to reduce their molecular weight. The gas phase recovered from the reactor zone effluent stream after hydrocarbon recovery may be partially recycled if it contains a sufficient quantity of hydrogen and/or carbon monoxide.

Without further elaboration, it is believed that one skilled in the art can, using the description herein, utilize the present invention to its fullest extent. The following specific embodiments are to be construed as illustrative and not as constraining the scope of the present invention in any way whatsoever.

EXAMPLES

General Procedure

Each of the catalyst samples was treated with hydrogen prior to use in the Fischer-Tropsch reaction. The catalyst sample was placed in a small quartz crucible in a chamber and purged with 500 sccm ($8.3 \times 10^{-6}$ m$^3$/s) nitrogen at room temperature for 15 minutes. The sample was then heated under 100 sccm ($1.7 \times 10^{-6}$ m$^3$/s) hydrogen at 1° C./minute to 100° C. and held at 100° C. for one hour. The catalysts were then heated at 1° C./minute to 400° C. and held at 400° C. for four hours under 100 sccm ($1.7 \times 10^{-6}$ m$^3$/s) hydrogen. The samples were cooled in hydrogen and purged with nitrogen before use.

A 2 mL pressure vessel was heated at 200° C. or 225° C. under 1000 psig (6994 kPa) of H$_2$:CO (2:1) and maintained at that temperature and pressure for 6 hours for the 200° C. runs and for 1 hour for the 225° C. runs. In a typical run, roughly 50 mg of the reduced catalyst and 1 mL of n-octane was added to the vessel. After one hour, the reactor vessel was cooled in ice, vented, and an internal standard of di-n-butylether was added. The reaction product was analyzed on an HP6890 gas chromatograph. Hydrocarbons in the range of C$_{11}$–C$_{40}$ were analyzed relative to the internal standard. The lower hydrocarbons were not analyzed since they are masked by the solvent and are also vented as the pressure is reduced.

The C$_{11}^+$ Productivity (g C$_{11}^+$/hour/kg catalyst) was calculated based on the integrated production of the C$_{11}$–C$_{40}$ hydrocarbons per kg of catalyst per hour. The logarithm of the weight fraction for each carbon number ln(W$_n$/n) was plotted as the ordinate vs. number of carbon atoms in (W$_n$/n) as the abscissa. From the slope, a value of alpha was obtained. As is known in the art, alpha is defined as the probability of hydrocarbon chain growth. Some runs displayed a double alpha as shown in Table 4. The results of runs over a variety of catalysts at 200° C. are shown in Table 2 and at 225° C. in Table 4.

Catalyst Preparation (Examples 1 through 6)

(NH$_3$)$_6$RuCl$_3$ was dissolved in H$_2$O in a Teflon® (polytetrafluoroethylene) beaker. The fluorided support was added to the beaker with stirring. The slurry was evaporated to dryness with stirring. The recovered solids were heated in argon for 3 hours at 350° C. The catalysts with nominal compositions as shown in Table 1 were isolated.

TABLE 1

| Example No. | (NH$_3$)$_6$RuCl$_3$ Weight in g | Fluoride (Wt., g) | Nominal Composition |
|---|---|---|---|
| 1 | 0.6127 | LaF$_3$ (1.800) | 10% Ru/LaF$_3$ |
| 2 | 0.6127 | YF$_3$ (1.800) | 10% Ru/YF$_3$ |
| 3 | 0.6127 | CrF$_3$ (1.800) | 10% Ru/CrF$_3$ |
| 4 | 0.6127 | ZnF$_2$ (1.800) | 10% Ru/ZnF$_2$ |
| 5 | 0.6127 | MgF$_2$ (1.800) | 10% Ru/MgF$_2$ |
| 6 | 0.6127 | CaF$_2$ (1.800) | 10% Ru/CaF$_2$ |

Support Preparation (Examples 1 through 6)

The preparation of the supports in Examples 1 through 6 will be illustrated by a description of the procedure for Example 1. The supports for Examples 2 through 6 are prepared in the same manner as Example 1, substituting the relevant oxide for La$_2$O$_3$ and adjusting the corresponding molar quantities of reagents. In Example 1 the support used was fluorided La$_2$O$_3$ prepared as follows. La(NO$_3$)$_3$.6H$_2$O (98.4 g) was dissolved in deionized water (1.5 L) in a 2 L breaker provided with an agitator. A solution (200 mL) of NH$_4$OH and deionized water (1/1, volume/volume was added during a period of 10 minutes to the agitated solution. The pH of the solution was 9.5 after this addition. The slurry was filtered and dried in air at 125° C. for about 18 hours, followed by calcination at 350° C. in air for an additional 8 hours. The product (46.8 g) was compressed into the wafers and screened. Lanthanum oxide particles in the 12×20 mesh (1.4 mm×0.83 mm) range were used. The granulated lanthanum oxide (15 mL) was placed in a 5/8" (1.58 cm) Inconel® nickel alloy reactor heated in a fluidized sand bath. It was heated to 175° C. in a flow of nitrogen (50 cc/min) at which time HF flow (50 cc/min) was also started through the reactor. As the initial exotherm monitored by an internal thermocouple subsided (2–3 hours), nitrogen flow decreased to 20 cc/min and HF flow increased to 80 cc/min. The reactor temperature was gradually increased to 400° C. during a 3–4 hour period and maintained at 400° C. for an additional 30 minutes, followed by cooling in nitrogen to room temperature.

TABLE 2

| Example | Catalyst | C$_{11}^+$Productivity | Alpha |
|---|---|---|---|
| 1 | 10% Ru/LaF$_3$ | 13.4 | 0.92 |
| 2 | 10% Ru/CrF$_3$ | 7.01 | 0.9 |
| 3 | 10% Ru/YF$_3$ | 5.56 | 0.94 |
| 4 | 10% Ru/ZnF$_2$ | 13.2 | 0.89 |
| 5 | 10% Ru/MgF$_2$ | 3.62 | 0.89 |
| 6 | 10% Ru/CaF$_2$ | 24.4 | 0.92 |

Catalyst Preparation (Examples 7 to 18)

(a) Powdered metal oxide (1 g) was placed into a clean quartz boat in a quartz tube furnace. A flow of hydrofluorocarbon HFC-152a (CF$_2$HCH$_3$) vapor of 100 cc/min. was established over the sample which was then heated to 450° C. at 20° C./min. (HFC-152a was used for all examples but 10 and 11. For those examples the catalyst was treated with HFC-23 (CHF$_3$)).

(b) After 1 hour at this condition, the sample was cooled and the tube flushed with nitrogen.

(c) The resulting fluorided metal oxide was slurried into a solution of a metal compound in a solvent (10 mL). The slurry was stirred thoroughly for 10 minutes and then evaporated to dryness.

(d) The dry solid was heated to 150° C. for 2 hours in flowing air after which it was heated to 400° C. in flowing nitrogen.

(e) Once at 400° C. the gas flush was switched to dry hydrogen and the sample was held at 400° C. in this reducing condition for 1 hour. The sample, the nominal composition of which is shown in Table 3, was cooled and collected under nitrogen and tested for Fischer-Tropsch (FT) activity.

For Examples 7, 8, 12, 13, 15, and 16 the $RuCl_3$ used in step (c) was dissolved in methanol.

For Example 11 the $RuCl_3$ used in step (c) was dissolved in water.

For Examples 9, 10, 11, 14, 17, and 18 the $Co_4(CO)_{12}$ used in step (c) was dissolved in toluene.

For Example 10 the $Pt(NH_3)_4Cl_2$ used in step (c) was dissolved in water.

For Example 9 in step (d) the dry solid was heated to 200° C. for 30 minutes in hydrogen.

For Example 10 step (c) was repeated for each metal compound; $Pt(NH_3)_4Cl_2$ was added first. Step (d) was the same as that used in Example 9.

For example 11 the procedure of Example 10 was followed and $RuCl_3$ replaced $Pt(NH_3)_4Cl_2$.

For Example 14, 17, and 18 the procedure of Example 10 was followed.

The results of runs, using the catalysts of Examples 7 to 18 in the Fischer-Tropsch synthesis at 225° C., following the General Procedures described above, are shown in Table 4.

TABLE 3

| Example No. | Metal Compound (Wt., g) | Metal Oxide | Nominal Composition (Wt. %) |
|---|---|---|---|
| 7 | $RuCl_3$ (0.04) | MgO | 1 wt % Ru/Fluorided MgO |
| 8 | $RuCl_3$ (0.4) | MgO | 10 wt % Ru/Fluorided MgO |
| 9 | $Co_4(CO)_{12}$ (0.5) | MgO | 20 wt % Co/Fluorided MgO |
| 10 | $Pt(NH_3)_4Cl_2$ (0.002) $Co_4(CO)_{12}$ (0.5) | MgO | 20 wt % Co/0.1 Wt % Pt/Flourided MgO |
| 11 | $RuCl_3$ (0.004) $Co_4(CO)_{12}$ (0.5) | MgO | 20 wt % Co/01. Wt % Ru/Fluorided MgO |
| 12 | $RuCl_3$ (0.04) | $TiO_2/Al_2O_3$ | 1 wt % Ru/Flourided $TiO_2/Al_2O_3$ |
| 13 | $RuCl_3$ (0.4) | $TiO_2/Al_2O_3$ | 10 wt % Ru/Fluorided $TiO_2/Al_2O_3$ |
| 14 | $Co_4(CO)_{12}$ (0.5) | $TiO_2/Al_2O_3$ | 20 wt % Co/Fluorided $TiO_2/Al_2O_3$ |
| 15 | $RuCl_3$ (0.04) | $ZrO_2$ | 1 wt % Ru/Fluorided $ZrO_2$ |
| 16 | $RuCl_3$ (0.4) | $ZrO_2$ | 10 wt % Ru/Fluorided $ZrO_2$ |
| 17 | $Co_4(CO)_{12}$ (0.5) | $ZrO_2$ | 20 wt % Co/Fluorided $ZrO_2$ |
| 18 | $Co_4(CO)_{12}$ (0.5) | CaO | 20 wt % Co/Fluorided CaO |

TABLE 4

| Example | Catalyst | $C_{11}^+$Productivity | Alpha |
|---|---|---|---|
| 7 | 1 wt % Ru/Fluorided MgO | 69 | 0.88 |
| 8 | 10 wt % Ru/Fluorided MgO | 28 | 0.87 |
| 9 | 20 wt % Co/Fluorided MgO | 95 | 0.86 |
| 10 | 20 wt % Co/0.1 Wt. % Pt/Fluorided MgO | 55 | 0.85 |
| 11 | 20 wt % Co/0.1 Wt. % Ru/Fluorided MgO | 110 | 0.82/0.93 |
| 12 | 1 wt % Ru/Fluorided $TiO_2/Al_2O_3$ | 21 | 0.78/0.87 |
| 13 | 10 wt % Ru/Flourided $TiO_2/Al_2O_3$ | 398 | 0.92 |
| 14 | 20 wt % Co/Fluorided $TiO_2/Al_2O_3$ | 549 | 0.90 |
| 15 | wt % Ru/Fluorided $ZrO_2$ | 77 | 0.91 |
| 16 | 10 wt % Ru/Fluorided $ZrO_2$ | 327 | 0.92 |
| 17 | 20 wt % Co/Fluorided $ZrO_2$ | 233 | 0.87 |
| 18 | 20 wt % Co/Fluorided CaO | 40 | 0.88 |

While a preferred embodiment of the present invention has been shown and described, it will be understood that variations can be made to the preferred embodiment without departing from the scope of, and which are equivalent to, the present invention. For example, the structure and composition of the catalyst can be modified and the process steps can be varied.

The complete disclosures of all patents, patent documents, and publications cited herein are incorporated by reference in their entirety. U.S. patent application Ser. No. 09/314,928 entitled Fischer-Tropsch Processes and Catalysts Using Fluorided Alumina Supports, filed May 19, 1999, and U.S. patent application Ser. No. 09/314,920 entitled Fischer-Tropsch Processes and Catalysts With Promoters, filed May 19, 1999, are incorporated by reference in their entirety.

The foregoing detailed description and examples have been given for clarity of understanding only. No unnecessary limitations are to be understood therefrom. The invention is not limited to the exact details shown and described, for variations obvious to one skilled in the art will be included within the invention by the claims.

What is claimed is:

1. A process for producing hydrocarbons, comprising contacting a feed stream comprising hydrogen and carbon monoxide with a catalyst in a reaction zone; said catalyst comprising at least one catalytic metal for Fischer-Tropsch reactions; and a support selected from the group consisting of fluorides and fluorided oxides of at least one element selected from the group consisting of the elements of Group 2 through 15 of the periodic table of elements and elements with atomic numbers 58 through 71.

2. The process of claim 1 wherein the catalytic metal is at least one metal selected from the group consisting of iron, cobalt, nickel, and ruthenium.

3. The process of claim 2 wherein the support is selected from the group consisting of fluorides and fluorided oxides of at least one element selected from the group consisting of zinc, magnesium, calcium, barium, chromium, yttrium, lanthanum, samarium, europium, and dysprosium.

4. The process of claim 3 wherein the catalytic metal is at least one metal selected from the group consisting of cobalt, nickel, and ruthenium, and the feed gas stream contains hydrogen and carbon monoxide in a molar ratio of about 2:1.

5. The process of claim 3 wherein the catalytic metal is iron and the feed gas stream contains hydrogen and carbon monoxide in a molar ratio of about 0.67:1.

6. The process of claim 3 wherein the support is a fluorided oxide wherein the atomic ratio of fluorine to oxygen is at least 0.001:1.

7. The process of claim 3 wherein the catalyst is prepared from a zero valent metal precursor.

8. The process of claim 3 wherein the catalyst is prepared from a molten metal salt.

9. The process of claim 1 wherein the support is a fluorided oxide prepared by treating an oxide with fluosilicic acid.

10. The process of claim 1 wherein the support is a fluorided oxide prepared by treating an oxide with a vaporizable fluorine-containing compound.

11. A process for producing hydrocarbons, comprising contacting a feed stream comprising hydrogen and carbon monoxide with a catalyst in a reaction zone at a temperature, pressure and space velocity effective to produce an effluent stream comprising hydrocarbons; said catalyst comprising at least one catalytic metal for Fischer-Tropsch reactions; and a support selected from the group consisting of fluorides and fluorided oxides of at least one element selected from the group consisting of the elements of Group 2 through 15 of the periodic table of elements and elements with atomic numbers 58 through 71.

12. The process of claim 11 wherein the catalytic metal is at least one metal selected from the group consisting of iron, cobalt, nickel, and ruthenium.

13. The process of claim 12 wherein the support is selected from the group consisting of fluorides and fluorided oxides of at least one element selected from the group consisting of zinc, magnesium, calcium, barium, chromium, yttrium, lanthanum, samarium, europium, and dysprosium.

14. The process of claim 13 wherein the catalytic metal is at least one metal selected from the group consisting of cobalt, nickel, and ruthenium, and the feed gas stream contains hydrogen and carbon monoxide in a molar ratio of about 2:1.

15. The process of claim 13 wherein the catalytic metal is iron and the feed gas stream contains hydrogen and carbon monoxide in a molar ratio of about 0.67:1.

16. The process of claim 13 wherein the support is a fluorided oxide wherein the atomic ratio of fluorine to oxygen is at least 0.001:1.

17. The process of claim 13 wherein the catalyst is prepared from a zero valent metal precursor.

18. The process of claim 13 wherein the catalyst is prepared from a molten metal salt.

19. The process of claim 11 wherein the support is a fluorided oxide prepared by treating an oxide with fluosilicic acid.

20. The process of claim 11 wherein the support is a fluorided oxide prepared by treating an oxide with a vaporizable fluorine-containing compound.

* * * * *